(12) United States Patent
Chen et al.

(10) Patent No.: US 7,968,726 B2
(45) Date of Patent: Jun. 28, 2011

(54) METHODS OF PREPARING IMIDAZOLE-BASED BICYCLIC COMPOUNDS

(75) Inventors: Jason Guohua Chen, Pudong Shanghai (CN); Weifeng Hu, Shanghai (CN); Renmao Liu, Pudong Shanghai (CN); Yuelie Lu, Shanghai (CN); Wenxue Wu, Princeton Junction, NJ (US); Xiaogen Yang, Shanghai (CN)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 12/485,507

(22) Filed: Jun. 16, 2009

(65) Prior Publication Data

US 2009/0318705 A1   Dec. 24, 2009

Related U.S. Application Data

(60) Provisional application No. 61/073,399, filed on Jun. 18, 2008.

(51) Int. Cl.
*C07D 413/04* (2006.01)
(52) U.S. Cl. ..................................... 548/247
(58) Field of Classification Search ............ 548/247
See application file for complete search history.

(56) References Cited

U.S. PATENT DOCUMENTS

| 4,567,194 A | 1/1986 | Kroeplien |
| 7,598,280 B2 * | 10/2009 | Augeri et al. ............... 514/365 |
| 7,649,098 B2 | 1/2010 | Augeri |
| 2008/0262241 A1 | 10/2008 | Wu |
| 2009/0030050 A1 * | 1/2009 | Augeri et al. ............... 514/365 |
| 2009/0312375 A1 * | 12/2009 | Augeri et al. ............... 514/365 |
| 2009/0318516 A1 | 12/2009 | Burgoon |

FOREIGN PATENT DOCUMENTS

| WO | WO 97/46543 | 12/1997 |
| WO | WO 2007/002458 | 1/2007 |
| WO | WO 2008109314 A1 * | 9/2008 |

OTHER PUBLICATIONS

Bagdanoff, J.T., et al., *J. Med. Chem.* 52:3941-3953 (2009).
Cliff and Pyne, *J. Org. Chem.*, 62: 1023-1032 (1997).
Cliff and Pyne, *Tett. Letters*, 36(33): 5969-5972 (1995).
Halweg and Buchi, *J. Org. Chem.* 50(7): 1134-6 (1985).
Pyne and Ung, *Synlett* 280-282 (1998).
Pyne, *ACGC Chem. Res. Comm.* 11:108-112 (2000).
Sweeny, J.R. et al., *J. Org. Chem.* 50:1133-1134 (1985).
PCT International Search Report and Written Opinion of the International Searching Authority dated Nov. 1, 2010, for International Application No. PCT/US2009/047495, filed Jun. 16, 2009.

\* cited by examiner

*Primary Examiner* — Joseph Kosack
*Assistant Examiner* — Matthew Coughlin
(74) *Attorney, Agent, or Firm* — Max Bachrach

(57) ABSTRACT

Methods of preparing compounds of formula I are disclosed:

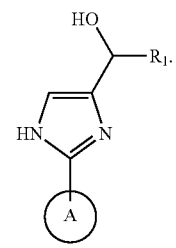

14 Claims, No Drawings

METHODS OF PREPARING IMIDAZOLE-BASED BICYCLIC COMPOUNDS

This application claims priority to U.S. provisional application No. 61/073,399, filed Jun. 18, 2008, the entirety of which is incorporated herein by reference.

1. FIELD OF THE INVENTION

This invention relates to methods of synthesizing compounds useful in the treatment of diseases and disorders of the immune system.

2. BACKGROUND

The compound 1-(4-((1R,2S,3R)-1,2,3,4-tetrahydroxybutyl)-1H-imidazol-2-yl)ethanone (THI) is a minor constituent of Carmel Color III, and reportedly lowers circulating lymphocyte counts in rats. Methods of preparing THI have been reported. See, e.g., Kroplien, U. and Rosdorfer, J., *J. Org. Chem.* 50:1131-1133 (1985); U.S. Pat. No. 4,567,194 to Kröplien et al.; Cliff, M. D. and Pyne, S. G., *Tet. Lett.* 36(33): 5969-5972 (1995); Cliff, M. D. and Pyne, S. G., *J. Org. Chem.* 62:1023-1032 (1997). A particular method reportedly provides THI in an overall yield of 46%. See Halweg, K. M. and Büchi, G., *J. Org. Chem.* 50:1134-1136, 1135 (1985).

It was recently reported that other imidazole-based compounds are potent inhibitors of immune response, and may be useful in the treatment of diseases such as rheumatoid arthritis. See U.S. patent application Ser. No. 12/038,872 to Augeri et al., filed Feb. 28, 2008. In order to facilitate their testing and use, additional methods of the compounds' synthesis are desired.

3. SUMMARY OF THE INVENTION

This invention encompasses methods of preparing compounds of formula I:

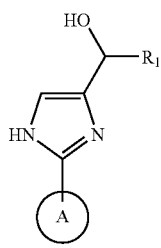

wherein: A is an optionally substituted heterocycle; $R_1$ is $N(R_{1A})_2$, hydrogen, hydroxy, or optionally substituted alkyl, aryl, alkylaryl, arylalkyl, heteroalkyl, heterocycle, alkylheterocycle, or heterocyclealkyl; and each $R_{1A}$ is independently hydrogen or optionally substituted alkyl, aryl, alkylaryl, arylalkyl, heteroalkyl, heterocycle, alkylheterocycle, or heterocyclealkyl.

4. DETAILED DESCRIPTION

Formula I encompasses S1P lyase inhibitors believed to be useful in the treatment of diseases and disorders such as rheumatoid arthritis. See U.S. patent application Ser. No. 12/038,872 to Augeri et al., filed Feb. 28, 2008. This invention encompasses synthetic methods suitable for the large-scale (e.g., kilogram scale) manufacture of those compounds.

4.1. DEFINITIONS

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl).

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A stereomerically pure composition of a compound that has multiple stereocenters, but which is drawn or named in such a way that the stereochemistries of less than all of its stereocenters are defined, is substantially free of the isomers of the compound that have different stereochemistries at the stereocenters for which stereochemistry is defined. For example, "stereomerically pure ((1R)-1,2-dichloropropyl)benzene" refers to ((1R)-1,2-dichloropropyl)benzene that is substantially free of ((1S)-1,2-dichloropropyl)benzene.

A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl- or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

In a particular embodiment, the term "substituted," when used to describe a chemical structure or moiety, refers to a derivative of that structure or moiety wherein one or more of its hydrogen atoms is substituted with one or more of: alkoxy, alkoxycarbonyl alkyl, amine, aryl, cyano, halo, haloalkyl, hydroxyl, or nitrile.

Unless otherwise indicated, the phrase "greater than X," where X is a number, has the same meaning as "X or greater than X." Similarly, the phrase "greater than about X," where X is a number, has the same meaning as "about X or greater than about X."

Unless otherwise indicated, the phrase "less than X," where X is a number, has the same meaning as "X or less than X." Similarly, the phrase "less than about X," where X is a number, has the same meaning as "about X or less than about X."

Unless otherwise indicated, the term "include" has the same meaning as "include" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl"

and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

4.2. METHODS OF SYNTHESIS

This invention encompasses methods of preparing compounds of formula I:

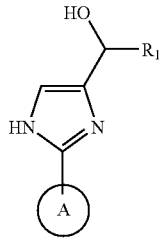

I wherein: A is an optionally substituted heterocycle; $R_1$ is $N(R_{1A})_2$, hydrogen, hydroxy, or optionally substituted alkyl, aryl, alkylaryl, arylalkyl, heteroalkyl, heterocycle, alkylheterocycle, or heterocyclealkyl; and each $R_{1A}$ is independently hydrogen or optionally substituted alkyl, aryl, alkylaryl, arylalkyl, heteroalkyl, heterocycle, alkylheterocycle, or heterocyclealkyl. In one embodiment, the compound is prepared by contacting a compound of formula II:

II with a compound of formula III:

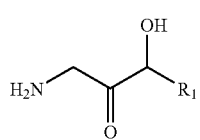

III under conditions sufficient for the formation of the compound of formula I.

In a particular embodiment, A is optionally substituted dihydro-imidazole, dihydro-isoxazole, dihydro-pyrazole, dihydro-thiazole, dioxolane, dithiolane, dithiole, imidazole, isoxazole, isoxazolidine, oxathiolane, or pyrazole.

Conditions sufficient for the formation of the compound of formula I include conducting the reaction in a solvent and in the presence of base. Examples of solvents include alcohols, such as methanol, ethanol, isopropanol, and ethers, such as tetrahydrofuran, methyl t-butyl ether, methyltetrahydrofuran, dimethoxyethane, and mixture thereof. Examples of bases include metal alkoxides, such as sodium methoxide (NaOMe), sodium ethoxide (NaOEt), and potassium t-butoxide (KOtBu).

In a particular method of the invention, a compound of formula I(a):

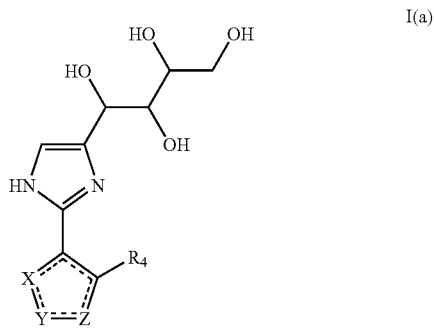

I(a)

is prepared by contacting a compound of formula II(a):

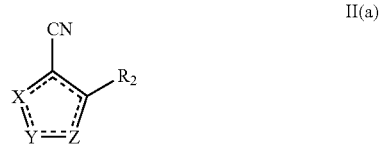

II(a)

with 1-amino-3,4,5,6-tetrahydroxyhexan-2-one:

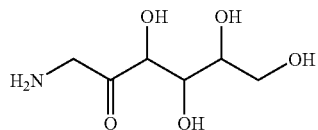

under conditions sufficient for the formation of the compound of formula I(a), wherein: X is $CR_2$, $CHR_2$, N, $NR_3$, O or S; Y is $CR_2$, $CHR_2$, N, $NR_3$, O or S; Z is $CR_2$, $CHR_2$, N, $NR_3$, O or S; each $R_2$ is independently $OR_{2A}$, $OC(O)R_{2A}$, hydrogen, halogen, or optionally substituted alkyl, aryl, alkylaryl, arylalkyl, heteroalkyl, heterocycle, alkylheterocycle, or heterocyclealkyl; each $R_{2A}$ is independently hydrogen or optionally substituted alkyl, aryl, alkylaryl, arylalkyl, heteroalkyl, heterocycle, alkylheterocycle, or heterocyclealkyl; and each $R_3$ is independently hydrogen or optionally substituted alkyl, aryl, alkylaryl, arylalkyl, heteroalkyl, heterocycle, alkylheterocycle, or heterocyclealkyl.

In one embodiment, X is N or O. In one embodiment, Y is N or O. In one embodiment, Z is CH. In one embodiment, $R_2$ is hydrogen or optionally substituted lower alkyl.

In one embodiment, the compound of formula II(a) is isoxazole-3-carbonitrile:

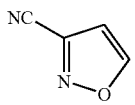

Isoxazole-3-carbonitrile may be prepared by contacting a compound of formula IV:

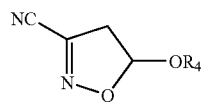
IV with a base under conditions sufficient to provide isoxazole-3-carbonitrile, wherein $R_4$ is alkyl. Examples of bases include inorganic bases (e.g., an alkali or alkali earth metal hydroxide, carbonate, phosphate, alkoxide or amide) and organic bases. Particular inorganic bases include sodium hydroxide, potassium carbonate, sodium hexamethyldisilazide (NaHMDS), and potassium t-butoxide. Particular organic bases include pyridine, triethylamine ($NEt_3$), diazabicyclo[5.4.0]undecene (DBU), diazabicyclo[5.4.0]nonene (DBN), and diisopropylethylamine. A specific base is DBU in tetrahydrofuran (THF) or dichloromethane (DCM).

The compound of formula IV may be prepared by contacting hydroxycarbonocyanidimidic chloride:

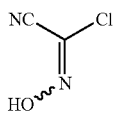

with alkoxy ethene under suitable reaction conditions.

Hydroxycarbonocyanidimidic chloride may be prepared by contacting N-hydroxy-2-(hydroxyimino)acetimidoyl chloride:

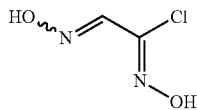

with a dehydrating agent (e.g., thionyl chloride ($SOCl_2$)) under suitable reaction conditions. Suitable reaction conditions include the presence of a solvent or solvent system, such as ethyl acetate (EtOAc), dimethylformamide (DMF), EtOAc/DMF, acetonitrile (MeCN)/DMF, DCM/$NEt_3$, methyl t-butyl ether (MTBE)/$NEt_3$, THF, THF/$NEt_3$, and THF/pyridine. A particular solvent is THF. A particular solvent system is THF/$NEt_3$.

N-hydroxy-2-(hydroxyimino)acetimidoyl chloride may be prepared by contacting chloral hydrate with hydroxylamine under conditions sufficient to provide N-hydroxy-2-(hydroxyimino)acetimidoyl chloride. Examples of such conditions include the presence of a base and a solvent or solvent system (e.g., water, ethanol, isopropanol, or THF). Particular bases include inorganic bases (e.g., alkali and alkali earth metal hydroxides, carbonates, phosphates, alkoxides or amides). Specific inorganic base are $K_2CO_3$, $Na_2CO_3$, NaOAc, KOAc, $KHCO_3$, and $K_3PO_4$.

A particular embodiment of the invention encompasses a method of preparing (1R,2S,3R)-1-(2-(isoxazol-3-yl)-1H-imidazol-5-yl)butane-1,2,3,4-tetraol:

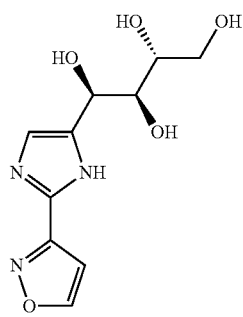

which comprises: combining isoxazole-3-carbonitrile with a solvent and a first base to provide a first reaction mixture; combining the first reaction mixture with fructosamine to provide a second reaction mixture; and isolating (1R,2S,3R)-1-(2-(isoxazol-3-yl)-1H-imidazol-5-yl)butane-1,2,3,4-tetraol from the second reaction mixture.

In a specific method, the second reaction mixture further comprises a second base. In a specific method, the solvent is methanol. In a specific method, the first base is the same as the second base. In a specific method, the first base is methoxide. In a specific method, the first and second bases are both methoxide.

This invention encompasses methods of preparing crystalline forms of (1R,2S,3R)-1-(2-(isoxazol-3-yl)-1H-imidazol-5-yl)butane-1,2,3,4-tetraol. In one method, a crystalline hydrate of (1R,2S,3R)-1-(2-(isoxazol-3-yl)-1H-imidazol-5-yl)butane-1,2,3,4-tetraol is obtained by cooling a solution comprising (1R,2S,3R)-1-(2-(isoxazol-3-yl)-1H-imidazol-5-yl)butane-1,2,3,4-tetraol and water to provide a precipitate, and isolating the precipitate. In one embodiment, the solution is at a temperature of from about 50 to about 100, about 60 to about 90, or about 70 to about 80° C. before cooling. In one embodiment, the solution is cooled to a temperature of less than about 25, 20 or 15° C. In a particular method, the isolated precipitate is washed with water or an alcohol (e.g., ethanol).

In one method, crystalline anhydrous (1R,2S,3R)-1-(2-(isoxazol-3-yl)-1H-imidazol-5-yl)butane-1,2,3,4-tetraol is obtained by cooling a solution comprising (1R,2S,3R)-1-(2-(isoxazol-3-yl)-1H-imidazol-5-yl)butane-1,2,3,4-tetraol and an alcohol (e.g., ethanol) to provide a precipitate, and isolating the precipitate. In one embodiment, the solution is at a temperature of from about 65 to about 80, about 70 to about 80, or about 75 to about 80° C. before cooling. In one embodiment, the solution is cooled to a temperature of less than about 25, 20 or 15° C. In a particular method, the isolated precipitate is washed with an alcohol (e.g., ethanol).

5. EXAMPLES

Aspects of this invention can be understood from the following examples.

5.1. Preparation of (1Z,2E)-N-hydroxy-2-(hydroxyimino)-acetimidoyl chloride

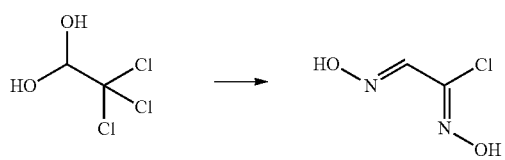

To a dried 50 L three-necked flask equipped with a thermometer controller, a mechanical stirrer, and a dropping funnel protected under nitrogen was charged 6060 g (2.4×) of water and 3151 g (1.26x) of hydroxylamine hydrochloride. The reaction mixture was stirred at 20-25° C. for 10-30 minutes until the solids was dissolved. To the solution was added drop wise a clear solution of 3134 g (1.25x) of potassium carbonate and 28000 g (11.2x) of water over 30-50 minutes at 20-25° C. followed by 2500 g (1.0x) of chloral hydrate in portions at 20-28° C. After addition, the reaction mixture was stirred at 25-30° C. for 4-5 hours and deemed complete by HPLC. The reaction mixture was cooled to 0-5° C. followed by addition of 9673 g (3.87x) of 25% sodium hydroxide for 60-90 minutes at 0-5° C. After addition, the stirring mixture was acidified with 12200 g (4.89x) of 25% sulfuric acid at 0-5° C. until pH=3.0-3.5. The resulting mixture was extracted twice with 2775 g (1.11x) of methyl t-butyl ether. The combined organic layer was dried with 1000 g (0.4x) of sodium sulfate, filtered and then concentrated under low pressure to 1500 g (0.6x) volume, which was diluted by 2670 g (1.08x) of n-heptane and concentrated again to 1500 g (0.6x) volume. The resulting slurry was added 2670 g (1.08x) of n-heptane, and then cooled to 0-5° C. and kept at this temperature for 1 hour. After filtration, the wet cake was washed twice with 250 g (0.1x) of n-heptane. The wet cake was dried under vacuum for 48 hrs at 30-38° C. to yield 737.0 g of off-white solid (Assay 98.3%, purity: 99.2%, yield 40%). $^1$H NMR (DMSO-$d_6$, 400 MHz) δ 12.44 (s, 1H), 12.23 (s, 1H), 8.27 (s, 1H); $^{13}$C NMR (DMSO-$d_6$, 100 MHz) δ 143.19, 137.83; Elemental analysis: Found: C, 19.54; N, 22.30; H, 2.64. Calculated for $C_2H_3N_2O_2Cl$: C, 19.61; N, 22.87; H, 2.47.

5.2. Preparation of 5-ethoxy-4,5-dihydroisoxazole-3-carbonitrile

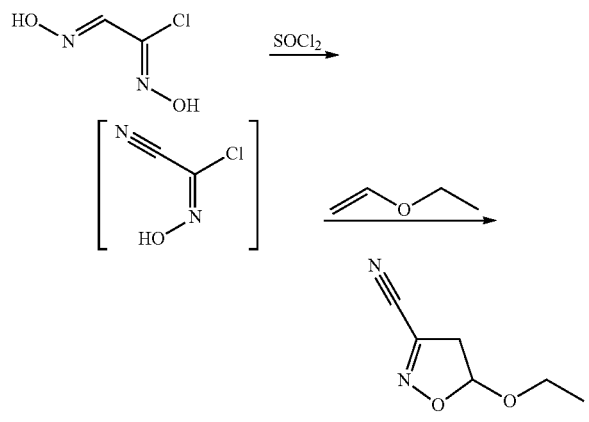

To a dried 10 L three-necked flask equipped with a thermometer controller, a mechanical stirrer, and a dropping funnel protected under nitrogen was charged 6966.7 g (7.3x) of tetrahydrofuran and 950.0 g (1.0x) of compound (1Z,2E)-N-hydroxy-2-(hydroxyimino)acetimidoyl chloride. The reaction mixture was cooled to 0-5° C. followed by drop wise addition of 1845.2 g (1.9x) thionyl chloride over 60~90 minutes at 0-5° C. After addition, the reaction mixture was stirred at 10-15° C. for 6-7 hours and deemed complete by HPLC. The reaction mixture was then concentrated under vacuum at 15-20° C. to about 1.0 L (1.0x) followed by addition of a total of 950 g (0.9x) of tetrahydrofuran and distillation to remove residual thionyl chloride. The resulting mixture was added drop wise into a solution of 2755 g (2.9x) of ethoxyethene, 6764 g (7.12x) of tetrahydrofuran and 715.0 g (0.75x) of sodium carbonate in 3200.0 g (3.4x) of water over 30-40 minutes at 0-5° C. After addition, the reaction mixture was stirred at 0-5° C. for 1-2 hours and deemed complete by HPLC. The resulting mixture was separated and the aqueous layer was extracted with 1900 g (2.0x) of methyl t-butyl ether, and then the combined organic layer was dried with 380 g (0.4x) of sodium sulfate, filtered and then concentrated to give 549.7 g yellow oil (Assay 60.3%, purity 97.0%, yield 30.5%). $^1$H NMR (CDCl$_3$, 400 MHz) δ 5.76 (dd, J=2.0 Hz, 4.8 Hz, 1H), 3.86~3.90 (m, 1H), 3.60~3.65 (m, 1H), 3.21 (dd, J=6.8 Hz, 11.2 Hz, 1H), 3.00 (dd, J=2.0 Hz, 16 Hz, 1H), 1.21 (T, J=6.8 Hz, 1H).

5.3. Preparation of isoxazole-3-carbonitrile

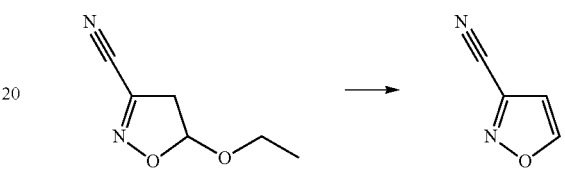

To a dried 10 L three-necked flask equipped with a thermometer controller, a mechanical stirrer, and a dropping funnel protected under nitrogen was charged 52000 g (18.6x) of dichloromethane and 289.8 g (1.0x, 449.3 g assayed at 64.5 wt %, 289.8 g real) of 5-ethoxy-4,5-dihydroisoxazole-3-carbonitrile. The reaction mixture was cooled to 0-5° C. followed by drop wise addition of 173.8 g (0.6x) of diazabicyclo[5.4.0]undecene for 20-30 minutes at 0-5° C. After addition, the reaction mixture was stirred at 0-5° C. for 2-3 hours and deemed complete by HPLC. The stirring mixture was neutralized with 1000.0 g (3.45x) of 0.1N hydrogen chloride at 0-5° C. to pH 6.5-7.0. The resulting mixture was extracted twice with 1170 g (4.0x) of methyl t-butyl ether. After separation, the combined organic layer was dried with 116 g (0.4x) of sodium sulfate, filtered and then concentrated under vacuum to give the crude isoxazole-3-carbonitrile (544.6 g assayed 21.99 wt %, 119.8 g real, 62% yield). Subsequent distillation (40° C./5 mmHg) gave 97.3 g of colorless oil (Purity 99%, yield 50%). $^1$H NMR (CDCl$_3$, 400 MHz) δ 8.64 (d, J=1.6 Hz, 1H), 6.70 (d, J=1.6 Hz, 1H); $^{13}$C NMR (CDCl$_3$, 100 MHz) δ 160.92, 139.19, 109.95, 107.40; Elemental analysis: Found: C, 50.02; N, 27.74, H 2.18. Calculated for $C_4H_2N_2O$: C, 51.07; N, 29.78; 2.14.

5.4. Preparation of (1R,2S,3R)-1-(2-(isoxazol-3-yl)-1H-imidazol-4-yl)butane-1,2,3,4-tetraol

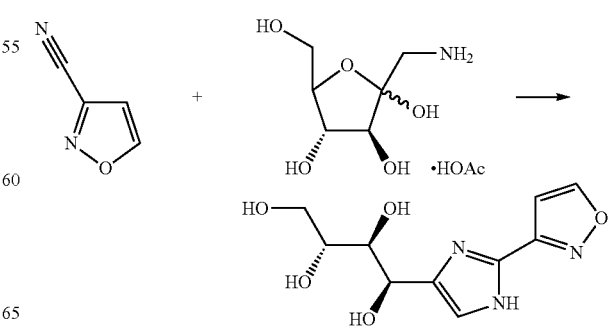

To a dried 10 L three-necked flask equipped with a thermometer controller, a mechanical stirrer, and a dropping funnel protected under nitrogen was charged 336.2 g (1.0×) of isoxazole-3-carbonitrile and 4125.0 g (12.3×) of methanol. To the stirring solution was added 449.2 g (1.34×) of sodium methoxide in methanol (25-30 wt %) over 15 min. The mixture was stirred at 20-25° C. overnight. The above solution was transferred into a slurry of 880.68 g (2.62×) of fructosamine acetic acid salt in 4125 g (12.3×) of methanol over 15 minutes and the mixture was stirred at 20-25° C. for 6 h. Another 400.0 g (1.2×) of sodium methoxide in methanol (25-30 wt %) was then added to the mixture over 10 minutes and the mixture was stirred for additional 6 h and deemed complete by HPLC. The reaction mixture was then diluted with 3362.3 g (10.0×) of water and concentrated under pressure to remove methanol, filtered and the cake was washed twice with 243.2 g (0.7×) of water to yield 1140 g of off-white solid (Purity 99.0%, assay 60%).

5.5. Crystallization of (1R,2S,3R)-1-(2-(isoxazol-3-yl)-1H-imidazol-4-yl)butane-1,2,3,4-tetraol hydrate Five grams of the dihydrochloride salt of (1R,2S,3R)-1-(2-(isoxazol-3-yl)-1H-imidazol-4-yl)butane-1,2,3,4-tetraol were dissolved in 50 mL water to provide a clear solution. To this solution was added 1M sodium hydroxide until the pH reached about 10 and solids precipitated. The solids were filtered and collected to obtain 5.6 g of (1R,2S,3R)-1-(2-(isoxazol-3-yl)-1H-imidazol-4-yl)butane-1,2,3,4-tetraol freebase wet cake.

To the wet cake from above was added 50 mL of water (10×), and the resulting mixture was heated to 70-75° C. to provide a clear tan solution. Upon cooling, solids began to crystallize out of solution. Further cooling caused more solids to crystallize until the stirring became problematic. At this point the solids were filtered, collected (2.36 g of free base) and dried under vacuum overnight at 50° C. Upon further cooling the filtrate produced a second crop of crystals.

5.6. Crystallization of Anhydrous (1R,2S,3R)-1-(2-(isoxazol-3-yl)-1H-imidazol-4-yl)butane-1,2,3,4-tetraol (1R,2S,3R)-1-(2-(isoxazol-3-yl)-1H-imidazol-4-yl)butane-1,2,3,4-tetraol hydrate (726 g) was heated in 7200.0 g (10.0×) of ethanol for 3-3.5 h at 75-80° C., and then cooled slowly to 10-15° C. and stirred for 2-2.5 h at 10-15° C. The solids were filtered, washed with 726 g (10×) of ethanol and dried under vacuum for 20 hrs at 30-40° C. to yield 663 g of anhydrous (1R,2S,3R)-1-(2-(isoxazol-3-yl)-1H-imidazol-4-yl)butane-1,2,3,4-tetraol as off-white solid. $^1$H NMR (DMSO-$d_6$ with a drop of DCl, 400 MHz) δ 8.71 (t, J=0.8 Hz, 1H), 7.40 (s, 1H), 6.89 (t, J=0.8 Hz, 1H), 5.06 (d, J=1.2 Hz, 1H), 3.53-3.69 (m, 3H), 3.49-3.52 (m, 1H); $^{13}$C NMR (DMSO-$d_6$ with a drop of DCl, 100 MHz) δ 163.2, 149.6, 139.0, 133.0, 118.5, 104.8, 73.4, 71.4, 65.2, 63.8; Elemental analysis: Found: C, 44.50; N, 15.77; H, 5.39. Calculated for $C_{10}H_{13}N_3O_5$: C, 47.06; N, 16.46; H, 5.13.

All cited publications, patents, and patent applications are herein incorporated by reference in their entireties.

What is claimed is:

1. A method of preparing (1R,2S,3R)-1-(2-(isoxazol-3-yl)-1H-imidazol-5-yl)butane-1,2,3,4-tetraol:

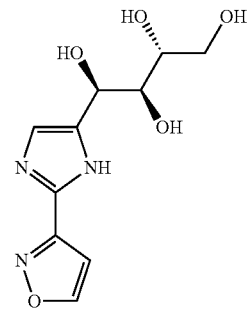

which comprises:
combining isoxazole-3-carbonitrile with a first solvent and a first base to provide a first reaction mixture;
combining the first reaction mixture with fructosamine to provide a second reaction mixture; and
isolating (1R,2S,3R)-1-(2-(isoxazol-3-yl)-1H-imidazol-5-yl)butane-1,2,3,4-tetraol from the second reaction mixture.

2. The method of claim 1, wherein the second reaction mixture further comprises a second base.

3. The method of claim 1, wherein the first solvent is methanol.

4. The method of claim 2, wherein the first base is the same as the second base.

5. The method of claim 1, wherein the first base is methoxide.

6. The method of claim 4, wherein the first base and the second base are both methoxide.

7. The method of claim 1, wherein the first reaction mixture is stirred for less than about 48 hours.

8. The method of claim 1, wherein the first reaction mixture is maintained at a temperature of from about 10 to about 30° C.

9. The method of claim 1, wherein the second reaction mixture is stirred for less than about 48 hours.

10. The method of claim 1, wherein the second reaction mixture is maintained at a temperature of from about 10 to about 30° C.

11. The method of claim 1, wherein the isoxazole-3-carbonitrile is prepared by contacting 5-ethoxy-4,5-dihydroisoxazole-3-carbonitrile with a base in a second solvent to provide a third mixture.

12. The method of claim 11, wherein the second solvent is tetrahydrofuran or dichloromethane.

13. The method of claim 11, wherein the third mixture is stirred at a temperature of from about −5 to about 10° C.

14. The method of claim 11, wherein the third mixture is stirred for less than about 10 hours.

* * * * *